US00PP14178P29

(12) United States Plant Patent
Bradford

(10) Patent No.: US PP14,178 P2
(45) Date of Patent: Sep. 23, 2003

(54) PLUM TREE NAMED 'AUTUMN YUMMY'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/300,414

(22) Filed: Nov. 21, 2002

(51) Int. Cl.[7] ..... A01H 5/00

(52) U.S. Cl. ..... Plt./184

(58) Field of Search ..... Plt./184

*Primary Examiner*—Bruce R. Campell
*Assistant Examiner*—Susan B. McCormick

(57) ABSTRACT

The present invention relates to a plum tree, *Prunus salicina,* and more particularly to a new and distinct variety broadly characterized by a large size, vigorous, hardy, heavy blooming, pollen abundant, self-unfruitful, and usually productive tree. The present variety requires cross pollinization other plums that bloom during the mid to late season, such as 'Blackamber' (unpatented) or 'Angeleno' (U.S. Plant Pat. No. 2,747). The fruit matures under the ecological conditions described in early September, with first picking on Sep. 7, 2002. The fruit is uniformly large in size, globose to slightly oblate in shape, blackish red in skin color, mostly red in flesh color, clingstone in type, very firm and crisp in texture, and very good in flavor. The variety was developed as a first generation cross using 'Freedom' (unpatented) as the selected seed parent and an undetermined plum as the pollen parent.

1 Drawing Sheet

Botanical classification: *Prunus salicina.*
Variety denomination: 'Autumn Yummy®'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'Autumn Yummy®'. Yummy® is a U.S. Trademark, Ser. No. 75618722, owned by Johnny Appleseed Holdings Limited, Saint Georges Road South RD2, Hastings, New Zealand. Permission to use has been granted to the applicant by contract.

During a typical blooming season I isolate as seed parents both individual and groups of different plum trees by covering them with screen houses. A hive of bees is placed inside each such house and bouquets to provide pollen from different plum, apricot, and plum-apricot hybrid trees are placed near the trees approximately every three days for the duration of the bloom. During 1998 one such house with an individual tree of 'Freedom' (unpatented) was crossed by me in this manner. To pollinate this 'Freedom' tree, I selected bouquets from several sources that season without keeping written details. Upon reaching maturity the fruit from this 'Freedom' tree was harvested and the seeds were removed, cracked, stratified and germinated as a group with the label "House12". They were grown as seedlings on their own root in my greenhouse and, upon reaching dormancy, transplanted to a cultivated area of my experimental orchard at Bradford Farms near Le Grand, Calif. in Merced County (San Joaquin Valley). During the summer of 2000, the present variety was selected as a single plant from the group of seedlings described above. Therefore, the variety was developed as a first generation cross using 'Freedom' (unpatented) as the selected seed parent and an undetermined plum as the pollen parent. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Freedom' (unpatented), by being self-unfruitful and by producing plums that are dark purple to black in skin color, firm in texture, and fairly large in size, but is distinguished therefrom and an improvement thereon by producing plums that are mostly red instead of yellow in flesh color, that are sweeter in flavor, that are juicier, and that mature about twenty-five days later.

The present variety is most similar to 'Angeleno' (U.S. Plant Pat. No. 2,747) plum by being self-unfruitful and by producing plums that are nearly black in skin color, globose to oblate in shape, firm in texture, and mature in the late season, but is distinguished therefrom and an improvement thereon by producing plums that are larger in size, sweeter in flavor, juicier, and mostly red instead of pale yellowish green in flesh color.

SUMMARY OF VARIETY

The present plum variety is characterized by a large size, vigorous, hardy, and usually productive tree. Being self-unfruitful, the present variety requires cross pollinization from another plum that blooms during the mid to late season, such as 'Blackamber' (unpatented) or 'Angeleno' (U.S. Plant Pat. No. 2,747). The present variety's abundance of blossoms and pollen entices strong bee activity to facilitate pollination. The fruit matures under the ecological conditions described during early September, with first picking on Sep. 7, 2002. The fruit is uniformly large in size, globose to slightly oblate in shape, blackish red in skin color, mostly red in flesh color, clingstone in type, very firm and crisp in texture, and very good in flavor.

DRAWING

The accompanying photograph exhibits four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif., and was developed at the state of shipping ripe on Sep. 15, 2002, on the original tree during its fourth growing season. All major color code designations are by reference to the Inter-Society Color Council, National Bureau of Standards. Common color names are also used occasionally.

Tree

Size: Large, reaching a height of 13' [4.0 m.] and a spread of 7' [2.1 m.] after four growing seasons utilizing typical dormant pruning.

Vigor: Vigorous, responding typically to irrigation and fertilization. The variety grows about 4' [1.2 m.] of surplus top-growth during the spring and summer. The plant should be grown on a standard commercial rootstock for production purposes.

Growth: Upright and dense.

Form: Original tree was trained to a central leader system by pruning, multiplied trees were pruned to vase form.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-unfruitful, requiring cross pollination by a suitable mid to late seasonal blooming plum, such as 'Blackamber' (unpatented) or 'Angeleno' (U.S. Plant Pat. No. 2,747).

Bearing: Usually consistent, but some uncertainty exists if inclement weather is encountered during the blooming period.

Trunk:

- *Size.*—Medium, reaching a maximum diameter of 3" [76 mm.] after the fourth growing season.
- *Texture.*—Somewhat shaggy.
- *Bark color.*—Brownish gray [64. brGy] with Moderate yellowish brown [77. m.yBr] streaking and crevices.
- *Lenticels.*—Approximate Number Per Square Inch: 24. Color: Moderate orange yellow [71. m.OY]. Average Size: ¼" [6.4 mm.].

Branches:

- *Size.*—Diameter of limb is 1 7/16" [37 mm.] measured 12" from the central leader, typical of *Prunus salicina,* and dependent upon cultural practices and climatic conditions.
- *Texture.*—Smooth on first and second year wood, increasing roughness with age.
- *Color.*—1st Year Wood Topside: Grayish reddish orange [39. gy.rO]. 1st Year Wood Underside: Brilliant yellow green [116. brill.YG]. Older Wood: Moderate brown [58. m.Br].
- *Lenticels.*—Approximate Number Per Square Inch: 80. Color: Moderate orange yellow [71. m.OY]. Average size: 1/16" [1.6 mm.].

Leaves:

- *Size.*—Large. Average Length: 3¾" [95 mm.]. Average width: 2¾" [70 mm.].
- *Arrangement.*—Alternate.
- *Thickness. Medium.*
- *Form.*—Elliptical.
- *Apex.*—Acuminate.
- *Base.*—Acute, with an average angle base angle of 60 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ½" [12.7 mm.]. Average Thickness: 1/16" [1.6 mm.]. Color: Light yellow green [119. l.YG] with a Light grayish red [18. l.gy.R] tinge with exposure to sunlight.
- *Stipules.*—Number: 2 per leaf, up to 6 per growing tip. Average length: ¼" [6.4 mm.]. Color: Light yellow green [119. l.YG]. Color: Light yellow green [119. l.YG].
- *Glands.*—Number: Usually 2 per leaf. Position: Slightly alternate, usually positioned on the base of leaf blade near the petiole. Size: Small. Form: Globose. Color: Brilliant yellow green [116. brill.YG] turning Dark reddish brown [44. d.rBr] in the center with age.
- *Leaf buds.*—Conic.

Flower buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Color.*—White [263. White].

Flowers: Perfect, complete, perigynous, usually a single pistil, typically thirty or more stamens, five sepals and petal locations alternately positioned.

- *Average flower diameter.*—9/16" [14.3 mm.].
- *Number of petals.*—Usually 5.
- *Petal shape.*—Oval, slightly concave inwardly.
- *Petal margin.*—Slightly wavy.
- *Average petal diameter.*—¼" [6.4 mm.].
- *Average petal length.*—5/16" [7.9 mm.].
- *Petal apex.*—Rounded.
- *Petal base.*—Acute.
- *Petal color.*—White [263. White].
- *Anther color.*—Very orange yellow [66. v.OY] on the exterior with a Light yellow [86. l.Y] center.
- *Stigma color.*—Pale yellow green [121. p.YG].
- *Sepal color.*—Brilliant yellow green [116. brill.YG] with Moderate purplish red [258. m.pR] margins.
- *Sepal length.*—5/32" [4 mm.].
- *Sepal width.*—⅛" [3 mm.].
- *Average pistil length.*—⅜" [9.5 mm.].
- *Average stamen length.*—5/16" [7.9 mm.].
- *Fragrance.*—Moderate.
- *Pollen production.*—Abundant.
- *Blooming period.*—Medium to late compared with other varieties, a few days after 'Santa Rosa' (unpatented).
- *Onset of bloom.*—One percent on Feb. 28, 2002.

*Date of full bloom.*—Mar. 10, 2002.
*Duration of bloom.*—One to two weeks, dependent on ambient temperature.
*Number per cluster.*—Typically 3 to 5, up to 9 observed.

FRUIT

Maturity when described: Shipping ripe, Sep. 13, 2002.
Date of first picking: Sep. 7, 2002.
Date of last picking. Sep. 23, 2002.
*Size: Uniform, medium.*
*Average diameter axially.*—2 7/16" [61.9 mm.].
*Average diameter across suture plane.*—2 11/16" [68.3 mm.].
*Typical weight.*—6.3 ounces [179 grams].
Form: Uniform, very symmetrical, globose to slightly oblate.
*Longitudinal section form.*—Elliptical, compressed axially.
*Transverse section through diameter.*—Circular.
Suture: A inconspicuous line located in a shallow groove extending from the base to just beyond the apex.
Ventral surface: Rounded, very slightly lipped toward the base.
Lips: Equal.
Cavity: Flaring, circular to slightly elongated in the suture plane, suture showing on one side.
*Depth.*—7/16" [11.1 mm.].
*Breadth.*—1 1/16" [27.0 mm.].
Base: Truncate, but slightly cuneate when viewed along the suture.
Apex: Rounded to somewhat truncate.
Pistil point: An inconspicuous.
Stem: Medium.
*Average length.*—3/8" [9.5 mm.].
*Average width.*—3/32" [2.4 mm.].
Skin:
*Thickness.*—Medium.
*Surface.*—Smooth.
*Tenacity.*—Tenacious to flesh.
*Astringency.*—Slight.
*Tendency to crack.*—Moderate from rapid growth, slight from wet conditions.
*Color.*—Blackish red [21. blackish R] over a Dark red [16. d.R] background with Light yellowish brown [76. l.yBr] freckling over the. entire surface.
*Bloom.*—Abundant.
Flesh:
*Color.*—Light orange yellow [70. l.OY] with an abundance of Moderate red [15. m.R] flecking and streaking throughout.
*Surface of pit cavity.*—Very deep red [14. v.deep R] fibers breaking away from the stone when twisted strongly.
*Amygdalin.*—Moderate.
*Juice.*—Abundant, rich.
*Texture.*—Very firm, very crisp.
*Fibers.*—Abundant, fine.
*Ripens.*—Fairly even.
*Flavor.*—Acidic and sweet, typically 17 to 21 brix.
*Aroma.*—Moderate.
*Eating quality.*—Very good.

STONE

Type: Clingstone.
Form: Oval.
Hilum: Very narrow.
Base: Somewhat oblique.
Apex: Obtuse, with an average angle of 110 degrees.
Sides: Equal.
Surface: Rough.
External color of stone: Light yellowish brown [76. l.yBr].
Pit wall color when cracked: Pale orange yellow [73. p.OY].
Cavity surface color: Grayish yellow [90. gy.Y].
Average pit wall thickness: 1/16" [1.6 mm.].
Average width: 11/16" [17.5 mm.].
Average length: 7/8" [22.2 mm.].
Average breadth: 3/8" [9.5 mm.].
Tendency to split: Very slight.
Kernel:
*Form.*—Oval.
*Pellicle color.*—Grayish brown [61. gy.Br].
*Skin color.*—Strong yellowish brown [74. s.yBr].
*Vein color.*—Dark yellowish brown [78. d.yBr].
*Taste.*—Slightly bitter.
*Viable.*—Yes.
*Average width.*—7/16" [11.1 mm.].
*Average length.*—9/16" [14.3 mm.].
*Amygdalin.*—Moderate to slight.

USE

Market: Fresh market and long distance shipping.
Keeping quality: Excellent. Fruit quality observed to remain in good condition in after 21 days in standard cold room at 36° Fahrenheit [2° Celsius].
Shipping quality: Excellent.
Resistance to insects: No unusual susceptibilities noted.
Resistance to diseases: No unusual susceptibilities noted.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'Angeleno' (U.S. Plant Pat. No. 2,747) plum by being self-unfruitful and by producing plums that are nearly black in skin color, globose to oblate in shape, firm in texture, and mature in the late season, but is distinguished therefrom and an improvement thereon by producing plums that are larger in size, sweeter in flavor, juicier, and mostly red instead of pale yellowish green in flesh color.

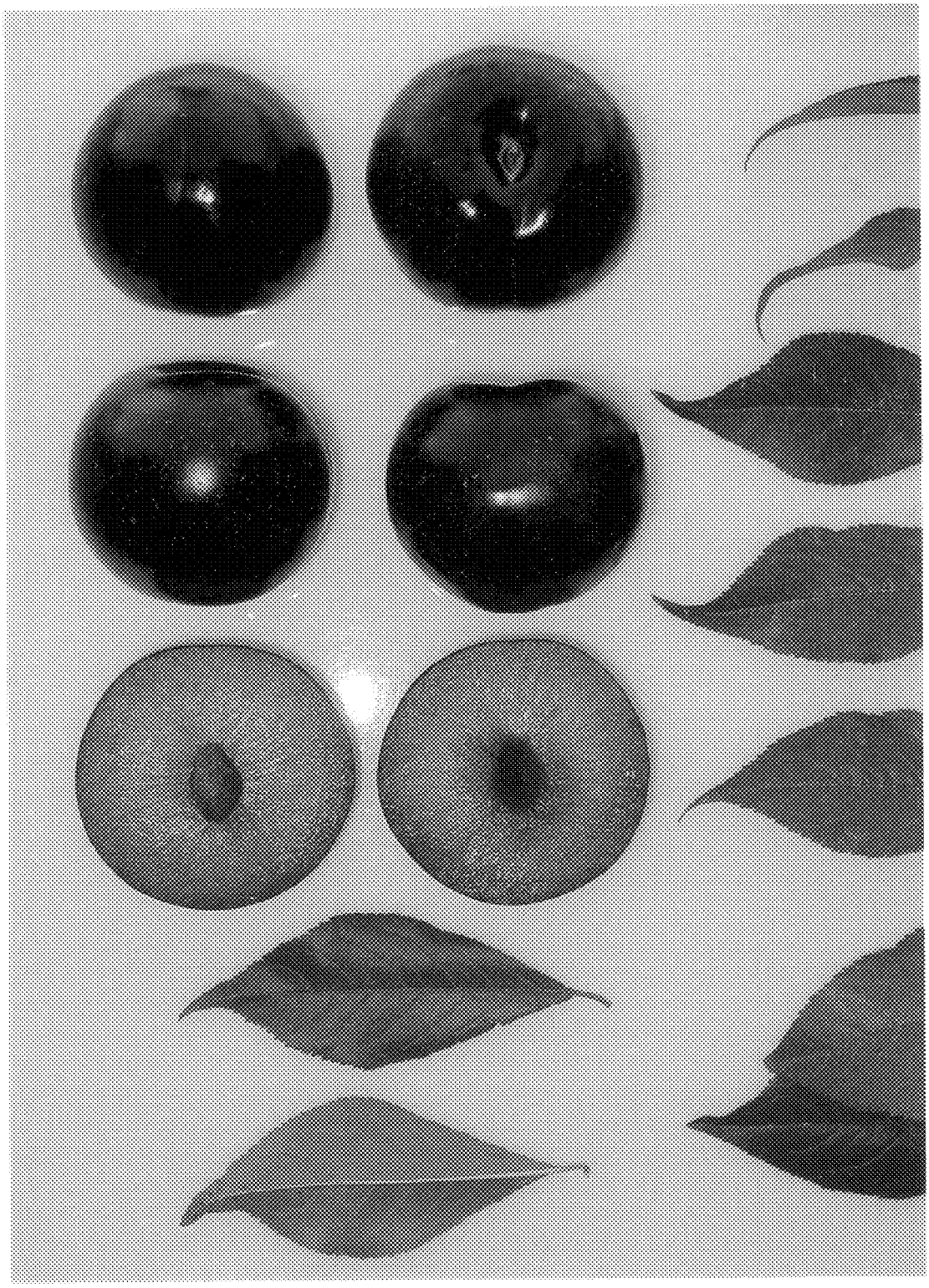

* * * * *